US00PP20226P3

(12) United States Plant Patent
Southwick et al.

(10) Patent No.: US PP20,226 P3
(45) Date of Patent: Aug. 18, 2009

(54) APRICOT TREE NAMED 'AC1'

(50) Latin Name: *Prunus armeniaca L.*
Varietal Denomination: AC1

(75) Inventors: Stephen M. Southwick, Lodi, CA (US); David Decalo, Boulder, CO (US)

(73) Assignee: SDR Fruit, LLC, Boulder, CO (US)

( * ) Notice: Subject to any disclaimer, the term of this patent is extended or adjusted under 35 U.S.C. 154(b) by 31 days.

(21) Appl. No.: 12/002,402

(22) Filed: Dec. 17, 2007

(51) Int. Cl.
*A01H 5/00* (2006.01)

(52) U.S. Cl. ..... Plt./186
(58) Field of Classification Search ..... Plt./186
See application file for complete search history.

*Primary Examiner*—Susan B Mccormick Ewoldt
(74) *Attorney, Agent, or Firm*—Wells St. John P.S.

(57) ABSTRACT

A new and distinct variety of apricot tree, denominated varietally as 'AC1' is disclosed and which is mature for harvesting and shipment under the ecological conditions prevailing in the San Joaquin Valley of California about April 30$^{th}$ to May 7$^{th}$.

4 Drawing Sheets

Latin name: *Prunus armeniaca* L.

BACKGROUND OF THE NEW VARIETY

The present invention relates to a new and distinct variety of apricot tree, '*Prunus armeniaca* L' and which has been denominated varietally as 'AC1', hereinafter, and more specifically to an apricot tree variety which is characterized as to novelty by bearing medium to large fruit which ripen early in the season, and which are further resistant to cracking as may be occasioned from being exposed to rain, and which further has a smooth skin and a bright orange-red blush, and wherein the present variety is ripe for harvesting and shipment approximately April 30–May 7 under the ecological conditions prevailing in the San Joaquin Valley of California.

ORIGIN AND ASEXUAL REPRODUCTION

The present variety of apricot was originated by the inventors from a chance open pollinated apricot cultivar named 'OrangeRed' (unpatented) and which is sometimes referred to as 'Bhart' in Europe and which was found in a cultivated area in 1993. Open pollinated seed derived from the newly discovered chance open pollinated cultivar 'OrangeRed' was germinated, and planted in 1994, by the inventors at an orchard which is located in Vina, Calif., in the northern portion of the San Joaquin Valley. The resulting tree grown from the open pollinated seed derived from the earlier mentioned chance open pollinated cultivar of 'OrangeRed' showed promising characteristics and was thereafter selected for propagation. The inventors first observed fruit produced from the new variety of apricot tree during the 1996 and 1997 growing seasons. The new variety of apricot tree was first asexually reproduced by budding in 1998. In this regard, bud wood from the new variety was first budded onto 'Lovell' peach rootstock (unpatented). These second generation trees were planted on a ranch which is located near Bakersfield, Calif. in the southern portion of the San Joaquin Valley. These asexually reproduced trees have been continually observed and compared and contrasted with the original chance, open pollinated seedling and its been subsequently determined that the characteristics of the original chance open pollinated seedling have been transmitted to the subsequent asexually reproduced trees.

SUMMARY OF THE VARIETY

The new variety of apricot tree 'AC1' is characterized as to novelty and is otherwise deemed noteworthy by producing fruit which are ripe for commercial harvesting and shipment approximately April 30–May 7 under the ecological conditions prevailing in the San Joaquin Valley of California. As compared to the fruit harvested from 'OrangeRed' apricot trees growing in the same geographical region, the present variety is harvested about 10 days earlier at the same geographical location and further produces larger fruit in relative comparison to the 'OrangeRed' apricot trees growing in the same geographical location. Further, the tree of the present variety thrives under high summer temperatures, which sometimes exceed 45 degrees C., and additionally is a consistent producer of high quality fruit under the low chilling hours environmental conditions prevailing in such locations as Bakersfield, Calif.

BRIEF DESCRIPTION OF THE DRAWINGS

The accompanying drawings are color photographs of various aspects of the present plant. The colors are as nearly true as reasonably possible in color representations of this type. Due to chemical development, processing and printing, the leaves and fruit of the present tree may or may not be accurate when compared to the actual specimen. For this reason, future color references should be made to the color plates as provided by The Royal Horticultural Society Colour chart and other general color descriptions as provided for hereinafter.

DETAILED DESCRIPTION

Figure 1:
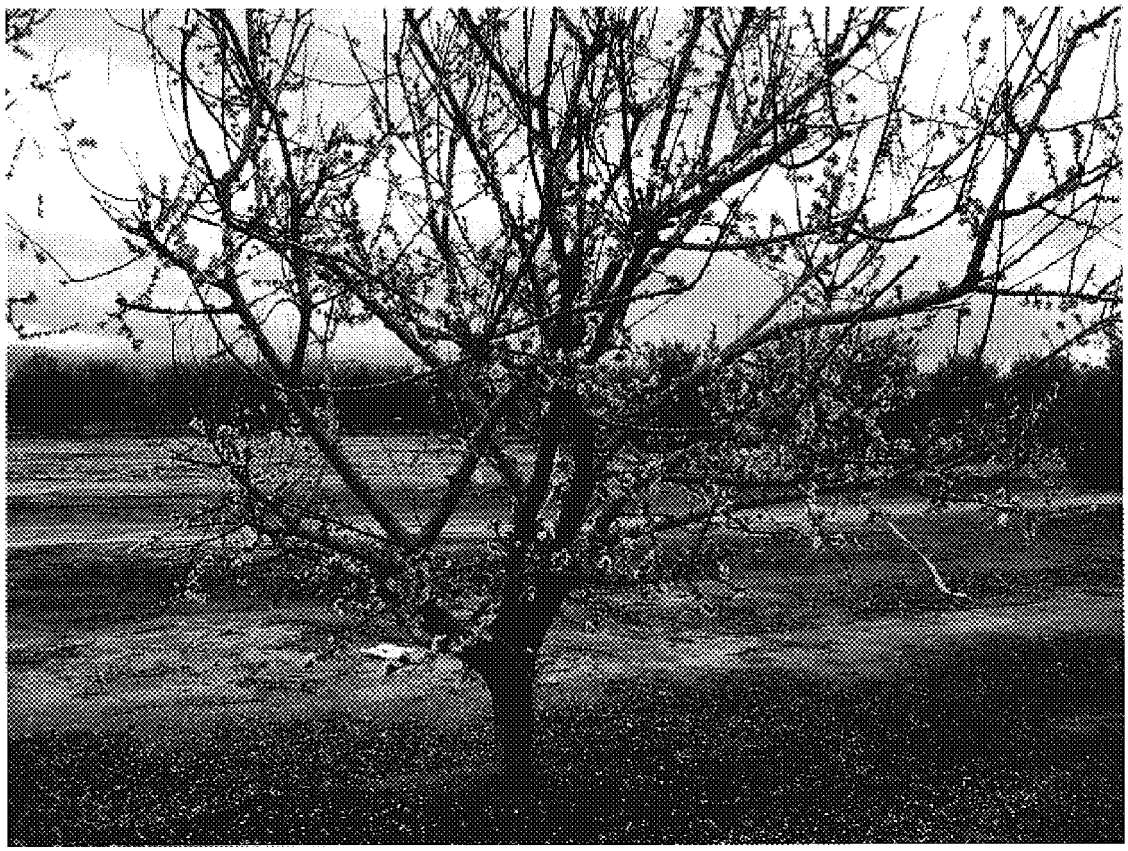
FIG. 1 illustrates the growing habit of a nine year old, second generation tree of the new variety of apricot tree as presently growing during the 2007 growing season near Bakersfield, Calif.
Figure 2:
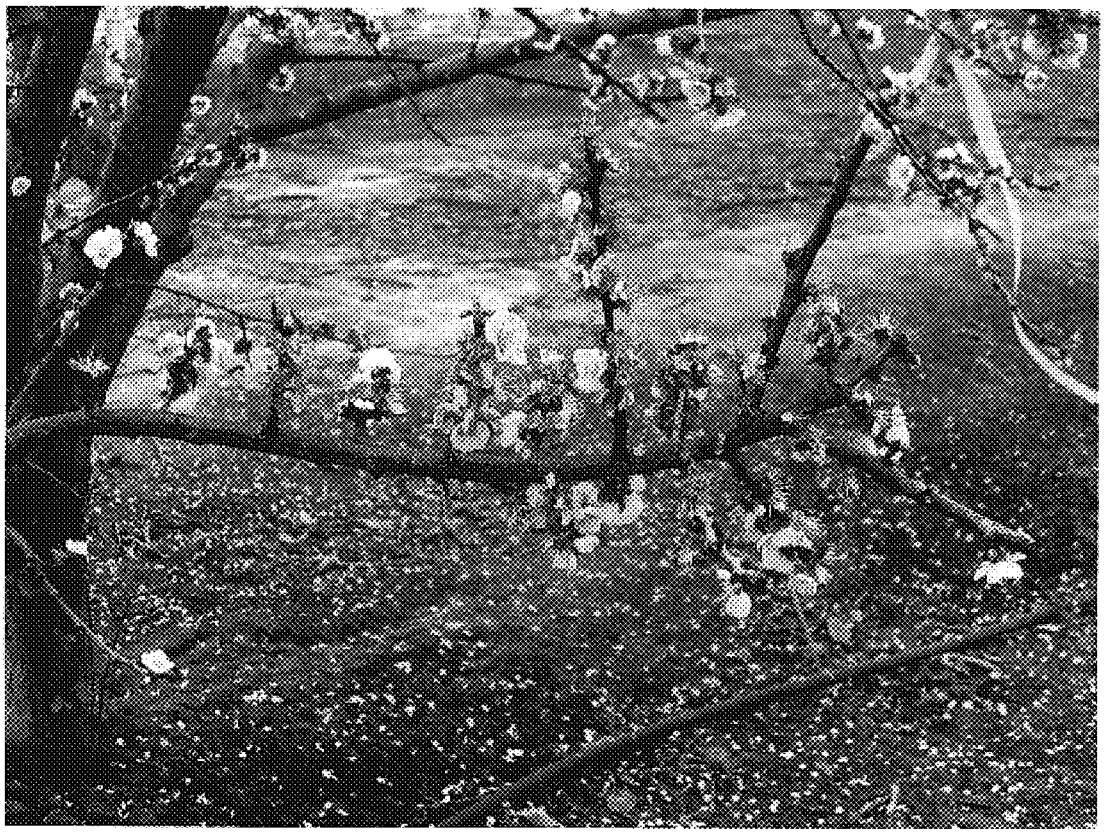
FIG. 2 shows the bloom characteristics of the 'AC1' apricot tree during the 2007 growing season.
Figure 3:
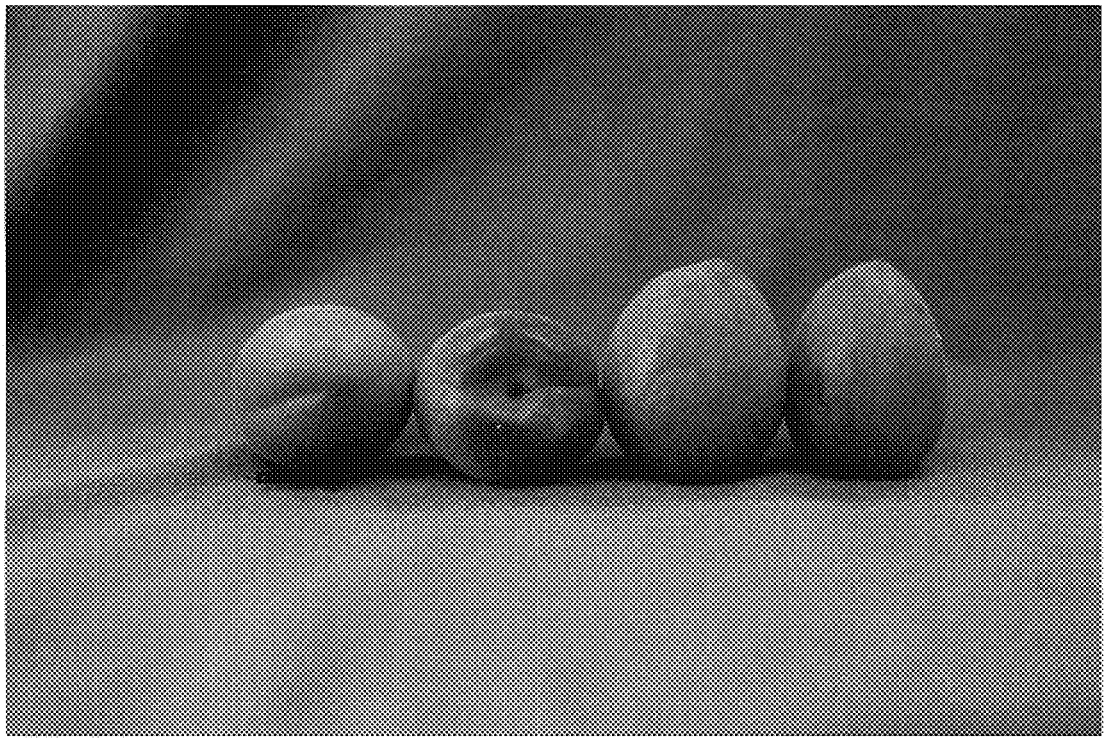
FIG. 3 shows several fruit of the present variety in several different orientations, and which are sufficiently matured for harvesting and shipment.
Figure 4:
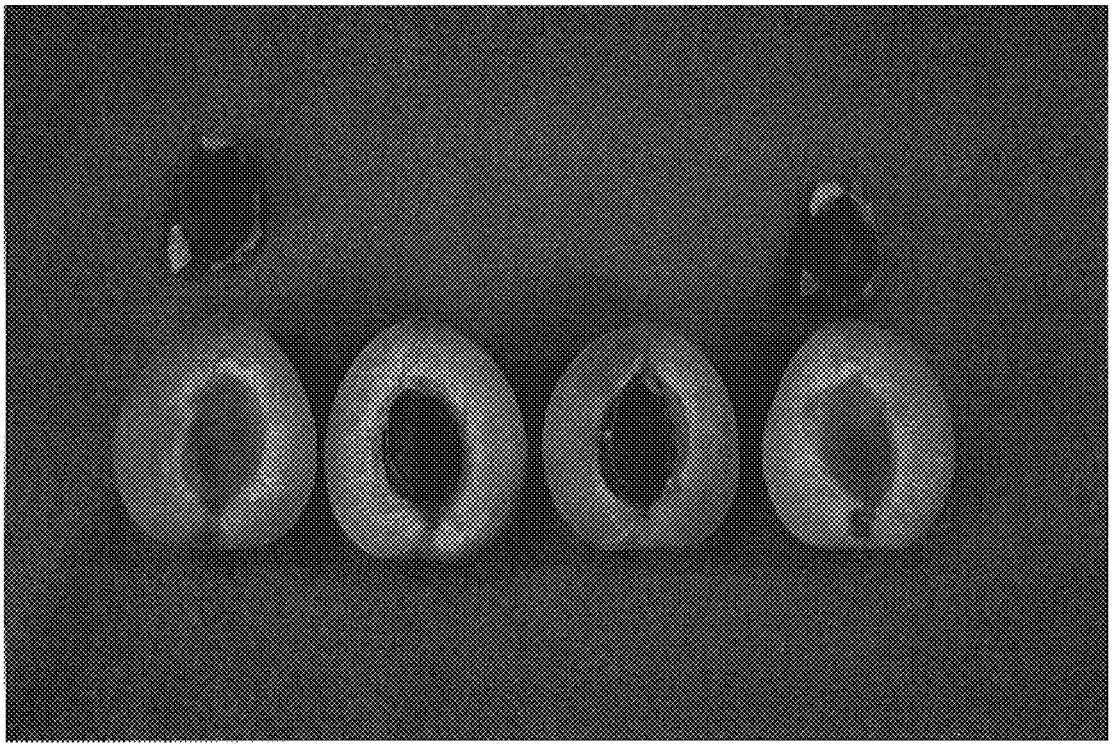
FIG. 4 shows several mature fruit of the subject variety which have been dissected in the axial plane to show the flesh and stone characteristics thereof.

Referring more specifically to the pomological details of this new and distinct variety of apricot tree, the following has been observed on a nine year old, second generation tree, under the ecological conditions prevailing at an orchard which is located near Bakersfield, Calif. All major color codes are by reference to the R.H.S. Colour Chart ($4^{th}$ Edition) provided by The Royal Horticultural Society of Great Britain. Common color names are also occasionally used.

NOT A COMMERCIAL WARRANTY

The following detailed description has been prepared to solely comply with the provisions of 35 U.S.C. §112, and does not constitute a commercial warranty, (either expressed or implied) that the present variety will in the future display the botanical pomological or other characteristics set forth hereinafter. Therefore, this disclosure may not be relied upon to support any future legal claims including, but not limited to, breach of warranty for merchantability, or fitness for any particular purpose which is directed, in whole or in part, to the present variety.

TREE

*Size.*—Considered average for the variety. The tree which was inspected was a nine year old second generation tree that had a height of about 5 meters; and a width dimension of approximately 3.5 meters.

*Vigor.*—Considered highly vigorous with an annual growth of about 0.25 meters to about 1 meter.

*Growth habit.*—Considered upright and spreading.

*Form.*—Upright and pruned into a vase shape.

*Productivity.*—Considered productive. Depending upon the fruit set of the tree, thinning may be required for fruit of the new tree to reach full commercial size.

*Regularity of bearing.*—Regular. This occurs even in seasons which have low chilling conditions.

*Fertility.*—The variety is not self-fertile, but requires cross-pollination from a compatible cultivar having approximately the same bloom time.

*Canopy density.*—Considered dense. The present variety requires seasonal pruning to maintain the vase shape, and keep the tree open for light penetration to maintain spur development and proper development of fruit to an appropriate commercial size.

*Hardiness.*—Considered hardy when grown under the ecological conditions prevailing in the San Joaquin Valley of California.

*Chilling requirements.*—About 500 to about 550 hours at a temperature below 7.2° C. to permit the variety to flower in a normal fashion.

TRUNK

*Diameter.*—About 30.5 cm. when measured about 30 cm. above the surface of the earth.

*Bark texture.*—Rough.

*Trunk bark color.*—The outer ridges of the bark color is black (Group 202 C); valleys in the bark are considered brown (Group N200B).

BRANCHES

*Scaffold branches.*—Generally — When measured at a distance of about 90 cm. above the soil line, the scaffold braches have a bark texture which is considered smooth, however, some outer layers will peel back in small concentric patches.

*Scaffold branch bark color.*—Brown (Group N200B).

*Lenticels.*—Generally — Present and considered numerous.

*Lenticels.*—Numbers — Generally 3 to 4 lenticels will be found per square cm.

*Lenticels.*—Size — About 2–3 mm. in width, and about 3–5 mm. in length.

*Lenticels.*—Color — Considered Brown (Group N200B).

*Flowering branches.*—Length — On average, these branches are about 75 cm. when measured at the end of the growing season.

*Flowering branches.*—Diameter — From about 4 mm. to about 4.6 mm.

*Flowering branches.*—Texture — Glabrous.

*Flowering branches.*—Color — Grey-orange (Group 177A).

*Flowering branches.*—Lenticels — Present and considered few to moderate in number, and ranging in count from about 5 to 10 lenticels per linear cm. as measured at approximately mid-point of a flowering branch.

*Lenticel color.*—White (Group 155D).

*Internodes.*—Length — Approximately 1.35 cm. to about 2.55 cm.

LEAVES

*Leaf form.*—Generally — Flat and broadly oval.

*Marginal form.*—Crenate and typically having 4 to 5 crenations per cm.

*Tip.*—Shape — Mucuronate and oriented to one side.

*Base.*—Shape — Rounded.

*Leaf size.*—Average length — About 94.1 mm.

*Leaf size.*—Width — About 72.5 mm.

*Leaf thickness.*—Average for the species.

*Leaf color.*—Upper surface — Green (Group 139A).

*Leaf color.*—Lower surface — Yellow-green (Group 147B).

*Petiole.*—Size — Average length, about 40.6 mm.

*Petiole.*—Diameter — About 1.62 mm.

*Petiole.*—Color — Yellow-green (Group 145D).

*Leaf glands.*—Shape — Globose in form, and having an average width of about 1 mm. and an average length of about 1.5 mm.

*Leaf glands.*—Position — Up to 2 leaf glands can typically be found per blade, and which are further located about 2 mm. to 15 mm. from the blade attachment.

*Leaf glands.*—Position — Alternate.

*Leaf glands.*—Color — Black (Group 202A).

*Leaf stipules.*—Absent.

*Leaf venation.*—Pinately net veined.

*Leaf buds.*—Shape — Ovoid.

*Leaf buds.*—Size — About 2.8 mm. wide, and about 3.8 mm. long.

*Leaf bud color.*—Considered Gray-purple (Group N186).

FLOWERS

*Date of first bloom.*—On or about Feb. 19, 2007 under the ecological conditions prevailing near Bakersfield, Calif.
*Date of full bloom.*—Feb. 24, 2007 under the ecological conditions prevailing near Bakersfield, Calif.
*Flower buds.*—Numbers — Usually 2 flower buds per node are observed.
*Flower buds.*—Shape — Ovoid.
*Flower buds.*—Size — About 3.1 mm wide, and about 4.5 mm long.
*Flower buds.*—Color — Gray-purple (Group N186).
*Flower size.*—At full expansion, the average diameter is about 2.4 cm.
*Flower aroma.*—Generally speaking, the aroma is present, but it is very slight.
*Flower petals.*—Numbers — 5.
*Flower petals.*—Arrangement — Considered overlapping.
*Flower petals.*—Shape — Flat-oval.
*Flower petals.*—Length — About 1.36 mm.
*Flower petals.*—Width — About 1.5 cm.
*Flower petals.*—Apex — The shape of the apex is considered rounded.
*Flower petals.*—Base — The shape of the base narrows at the attachment point.
*Flower petals.*—Surface Texture — Glabrous.
*Flower petals.*—Margins — Considered smooth.
*Flower petals.*—Color — White with a faint red-purple color on the apex (Group 69A).
*Sepals.*—Numbers — 5.
*Sepals.*—Shape — Oval with a cuspidate tip. The outer margins cup inwardly.
*Sepals.*—Length — About 5.9 mm.
*Sepals.*—Width — About 6.5 mm.
*Sepals.*—Surface texture — Considered glabrous.
*Sepals.*—Color — Red-purple (Group 60A).
*Stamens.*—Numbers — Variable from about 30 to 41.
*Stamens.*—Average length — About 10.4 mm.
*Stamens.*—Filament length — About 8.9 mm.
*Filament color.*—Green-white (Group 157D).
*Anther length.*—About 1.5 mm.
*Anther color.*—Yellow (Group 12B).
*Mature pollen color.*—Yellow (Group 12B).
*Pistil.*—Numbers — 1.
*Pistil.*—Length — About 1.49 cm.
*Ovary.*—Size — About 2.1 mm. in diameter; and about 3.2 mm. in length.
*Ovary color.*—Green (Group 140D).
*Ovary pubescence.*—Present.
*Stigma.*—Length — About 1.17 cm.
*Stigma.*—Color — Green-white (Group 157A).
*Thalamus.*—Size — About 4.2 mm in length, and about 4.7 mm. in width.
*Thalamus.*—Color — Green (Group 151D). Further, the base is highlighted with a red-purple color (Group 60A).

FRUIT

*Maturity.*—When described, firm, ripe condition, that is (shipping ripe). Date of first picking Apr. 30, 2007.
*Date of last pick.*—May 7, 2007. The aforementioned harvesting dates are under the ecological conditions prevailing near Bakersfield, Calif.
*Fruit size.*—Considered average for the species.
*Average length.*—About 54.6 mm.
*Average diameter.*—About 46.1 mm.
*Average diameter perpendicular to the fruit suture.*—About 41.9 mm.
*Fruit weight.*—The average fruit weight of the new variety is approximately 58 grams.
*Fruit shape.*—Generally speaking it is considered round, oblong, and slightly beaked.
*Stem cavity.*—Size — About 12.9 mm. wide; and about 8.7 mm. in depth.
*Fruit suture.*—Generally — Present, and shallow with a depth of less than about 1 mm.
*Fruit skin.*—Texture — Considered smooth.
*Fruit skin.*—Thickness — Considered thin for the species.
*Fruit skin.*—Pubescence — Present and very fine.
*Fruit skin.*—Color — The background color is orange (Group 26A). Additionally, a shoulder blush develops over the shoulder of the fruit and covers about 40%–50% of the skin area. This shoulder blush is orange-red (Group N34A).
*Tendency to crack.*—Not observed.
*Flesh texture.*—Considered tender and melting.
*Flesh.*—Color — Orange (Group 25B).
*Flesh.*—Sugar Content — On average, about 14.1 degrees brix.
*Flesh.*—Aroma — Considered typical of apricots.
*Flavor.*—Sweet and having a sub-acid character.
*Flesh fibers.*—Generally — Present, but sparse. The fibers are considered short and non-obtrusive.
*Eating quality.*—Considered excellent for both local and long distance commercial fresh markets.

STONE

*Generally.*—Considered to be a semi-clingstone.
*Stone length.*—About 28.8 mm.
*Stone diameter.*—Taken in the line of the suture, about 19.2 mm.
*Stone diameter.*—Taken at a position perpendicular to the suture, about 10 mm.
*Stone color.*—Fully dried — Grey-orange (Group 165A).
*Stone cavity.*—Length — About 31.9 mm.
*Stone cavity.*—Width — As measured at the suture, about 22.4 mm.
*Stone form.*—Generally — Considered ovate, and having equal halves when considered along the suture plane.
*Stone base.*—Shape — Rounded.
*Stone apex.*—Considered more conic than round.
*Stone ridges.*—Generally — Three distinct ridges extend from the apex to the base. Further, one or two shorter side ridges run from approximately one-half the distance starting at the base in the direction towards the apex. These additional shorter side ridges are located between the center and side ridges. The respective ridges are sharp and distinct.
*Stone surface.*—Surface Texture — Lightly textured.
*Tendency to split.*—The fruit which were inspected showed that about 30% of the stones had split at full commercial maturity.

*Resistance to insects and diseases.*—No particular susceptibilities were noted. The present variety has not been tested to expose or detect any susceptibilities or resistance of any known plant and/or fruit diseases.

Although the new variety of apricot possesses the described characteristics when grown under the ecological conditions prevailing in the San Joaquin Valley of California, it should be understood that variations of the usual magnitude and characteristics incident to changes in growing conditions, fertilization, pruning, pest control, and horticultural management are to be expected.

Having thus described and illustrated our new variety of apricot tree, what we claim is new, and desire to secure by Plant Letters Patent is:

1. A new and distinct variety of apricot tree substantially as shown and described and which is characterized principally as to novelty by having a date of harvesting which is about April $30^{th}$ to May $7^{th}$ under the ecological conditions prevailing in the San Joaquin Valley of California.

* * * * *